US006358681B2

(12) United States Patent
Ginsberg et al.

(10) Patent No.: US 6,358,681 B2
(45) Date of Patent: Mar. 19, 2002

(54) DIAGNOSTIC METHODS FOR ALZHEIMER'S DISEASE BY DETECTION OF MULTIPLE MRNAS

(75) Inventors: Stephen Ginsberg; John Q. Trojanowski; Virginia M.-Y. Lee; James Eberwine, all of Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 09/183,636

(22) Filed: Oct. 30, 1998

(51) Int. Cl.[7] ............................. C12Q 1/68; C12P 19/34

(52) U.S. Cl. .......................... 435/6; 435/91.1; 435/91.2

(58) Field of Search ........................... 435/6, 91.1, 91.2

(56) References Cited

PUBLICATIONS

Arai, H. et al., "Defined neurofilament, τ, and β–amyloid precursor protein epitopes distinguish Alzheimer from non–Alzheimer senile plaques", 1990 *Proc. Natl. Acad. Sci. USA* 87:2249–2253.

Arai, H. et al., "Expression Patterns of β–Amyloid Precursor Protein (β–APP) in Neural and Nonneural Human Tissues from Alzheimer's Disease and Control Subjects", 1991. *Ann. Neurol.* 30:686–693.

Ashburn et al., "Amyloid probes based on Congo Red distinguish between fibrils comprising different peptides", 1996 *Chemistry and Biology* 3:351–358.

Bahmanyar, S. et al., "Localization of Amyloid β Protein Messenger RNA in Brains from Patients with Alzheimer's Disease", 1987. *Science* 237:77–88.

Becker, I. et al., "Single–Cell Mutation Analysis of Tumors from Stained histologic Slides", 1996. *Lab. Invest.* 75:801–807.

Crino, P. B. and J. Eberwine, "Molecular Characterization of the Dendritic Growth Cone: Regulated mRNA Transport and Local Protein Synthesis", 1996. *Neuron* 17:1173–1187.

Crino, P. B. et al., "Embryonic neuronal markers in tuberous sclerosis: Single–cell molecular pathology", 1996. *Proc. Natl. Acad. Sci. USA* 93:14152–14157.

Dart, L. H. and T. R. Turner, "Fluorescence Microscopy in Exoliative Cytology", 1959. *Lab. Invest.* 8:1513–1522.

d'Amore, F. et al., "Molecular Studies on Single Cells Harvested by Micromanipulation from Archival Tissue Sections Previously Stained by Immunohistochemistry or Nonisotopic In Situ Hybridization", 1997 *Lab. Invest.* 76:219–224.

Eberwine, J. et al., "Analysis of gene expression in single live neurons", 1992. *Proc. Natl. Acad. Sci.* 89:3010–3014.

Emmert–Buck, M.R. et al., "Laser Capture Microdissection", 1996. *Science* 274:998–1001.

Ginsberg, S. D. et al., "The AMPA Glutamate Receptor gluR3 Is Enriched In Oxytocinergic Magnocellular neurons and is Localized at Synapses", 1995. *Neuroscience* 65:563–575.

Golde, T. E. et al., Expression of β Amyloid Protein Precursor mRNAs: Recognition of a Novel Alternatively Spliced Form and Quantitation in Alzheimer's Disease Using PCR 1990. *Neuron* 4:253–267.

Goldgaber, D. et al., "Characterization and Chromosomal Localization of a cDNA Encoding Brain Amyloid of Alzheimer's Disease", 1987. *Science* 235:877–880.

Hyman, B. T. et al., "Alzheimer's Disease: Cell–Specific Pathology Isolates the Hippocampal Formation", 1984 *Science* 225:1168–1170.

Hyman, B. T. et al., "Memory–related neural systems in Alzheimer's disease: An anatomic study", 1990 *Neurology* 40:1721–1730.

Hyman, B. T. et al., "Nonisotopic in situ hybridization of amyloid beta protein precursor in Alzheimer's disease: expression in neurofibrillary tangle bearing neurons and in the microenvironment surrounding senile plaques", 1993. *Mol. Brain Res.* 18:253–258.

Kang, J. et al., "The precursor of Alzheimer's disease amyloid A4 protein resembles a cell–surface receptor", 1987 *Nature* 325:733–736.

Kosik, K. S. et al., "Tau In Situ Hybridization in Normal and Alzheimer Brain: Localization in the Somatodendritic Compartment", 1989. *Ann. Neurol.* 26:353–361.

Lee, V. M.–Y et al., "A68: A Major Subunit of Paired Helical Filaments and Derivatized Forms of Normal Tau", 1991 *Science* 251:675–678.

MacGibbon, G. A. et al., "Bax expression in mammalian neurons undergoing apoptosis, and in Alzheimer's disease hippocampus", 1997. *Brain Res.* 750:223–234.

Mai, J. K. et al., "Use of Acridine Orange for Histologic Analysis of the Central Nervous System", 1984. *J. Histochem. Cytochem.* 32:97–104.

McMaster, G. K. and G. G. Carmichael, "Analysis of single–and double–stranded nucleic acids on polyacrylamide and agarose gels by using glyoxal and acridine orange", 1977. Proc. Natl. Acad. Sci. 74;4835–4838.

Mikel, U. V. and R. L. Becker, "A Comparative Study of Quantitative Stains for DNA in Image Cytometry", 1991. *Analyt. Quant. Cytol. Histol.* 13:253–260.

Mufson, E. J. et al., "Reduction in p140–TrkA Receptor Protein within the Nucleus Basalis and Cortex in Alzheimer's Disease", 1997, *Exp. Neurol.* 146:91–103.

Pinto, A. et al., "Acridine Orange–RNA Histofluorescence of Sarcomas and Small Round Cell Tumors of Childhood", 1990. *Arch. Pathol. Lab. Med.* 114(6) :585–588.

(List continued on next page.)

Primary Examiner—W. Gary Jones
Assistant Examiner—Jehanne Souaya
(74) Attorney, Agent, or Firm—Licata & Tyrrell P.C.

(57) ABSTRACT

Methods of detecting RNA in brain tissue of patients with Alzheimer's disease are provided. Methods of diagnosing Alzheimer's disease by detection of these RNAs are also provided.

2 Claims, No Drawings

OTHER PUBLICATIONS

Rigler, R., "Microfluorometric Characterization of Intracellular Nucleic Acids and Nucleoproteins by Acridine Orange", 1966. *Acta Physiol. Scand.* 67 (Suppl.) :7–122.

Robakis, N. K. et al., "Molecular cloning and characterization of a cDNA encoding the cerebrovascular and the neuritic plaque amyloid peptides", 1987. *Proc. Natl. Acad. Sci. USA* 84:4190–4194.

Salehi, A. et al., "Co–Localization of High–Affinity Neurotrophin Receptors in Nucleus Basalis of Meynert Neurons and Their Differential Reduction in Alzheimer's Disease", 1996. *Neurosci.* 75:373–387.

Schmechel, D. E. et al., "Cellular Localization of Messenger RNA Encoding Amyloid–Beta–Protein in Normal Tissue and in Alzheimer Disease", 1988. *Alzheim. Dis. Assoc. Disord.* 2:96–111.

Schmidt, M. L. et al., "Plaque–Associated Neuronal Proteins: A Recurrent Motif in Neuritic Amyloid Deposits throughout Diverse Cortical Areas of the Alzheimer's Disease Brain", 1994. *Exp. Neurol.* 130:311–322.

Schummelfeder, N., "Histochemical Significance of the Polychromatic Fluorescence Induced in Tissues Stained with Acridine Orange", 1958. *J. Histochem. Cytochem.* 6:392–393.

Schmued, L. C. et al., "Some Fluroescent Counterstains for Neuroanatomical Studies[1]", 1982. *J. Histochem. Cytochem.* 30:123–128.

Schmidt, M. L. et al., "Phosphate Dependent and Independent Neurofilament Epitopes in the Axonal Swellings of Patients with Motor Neuron Disease and Controls", 1987 *Lab. Invest.* 56:282–294.

Selkoe, D. J., "Cell Biology of the Amyloid β–Protein Precursor and the Mechanism of Alzheimer's Disease", 1994 *Annu. Rev. Cell Biol.* 10:373–403.

Selkoe, D. J., "Isolation of Law–Molecular–Weight Proteins from Amyloid Plaque Fibers in Alzheimer's Disease", et al. 1986. *J. Neurochem.* 46:1820–1834.

Strittmatter, W. J. and A. D. Roses, "Apolipoprotein E and Alzheimer disease", 1995. *Proc. Natl. Acad. Sci. USA* 92:4725–4727.

Su, J. H. et al., "Bax protein Expression is Increased in Alzheimer's Brain: Correlations with DNA Damage, Bcl–2 Expression, and Brain Pathology", 1997. *J. Neuropathol. Exp. Neurol.* 56:86–93.

Szabo, M. M. and E. Roboz–Einstein, "Acidic Polysaccharides in the Central Nervous System[1]", 1962. *Arch. Biochem. Biophys.* 98:406–412.

Tanzi, R. E. et al., "Amyloid β Protein Gene: cDNA, mRNA Distribution, and Genetic Linkage Near the Alzheimer Locus", 1987. *Science* 235:880–884.

Topaloglu, H. and H. B. Sarnat, "Acridine Orange–RNA Fluorescence of Maturing Neurons in the Perinatal Rat Brain", 1989. *Anat. Rec.* 224:88–93.

Trojanowski, J. Q. et al. 1996 In: *Current Neurology*, vol. XVI, Boston: Houghton Mifflin.

VanGelder, R. et al., "Amplified RNA synthesized from limited quantities of heterogeneous cDNA", 1990. *Proc. Natl. Acad. Sci. USA* 87:1663–1667.

von Bertalanffy, L. and I. Bickis, "Identification of Cytoplasmic basophilla (Ribonucleic Acid) By Fluorescence Microscopy[1]", 1956. *J. Histochem. Cytochem.* 1956. 4:481–493.

SEQUENCE LISTING

<160> NUMBER OF SEQ ID NOS: 3

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic

<400> SEQUENCE: 1
aaacgacggc cagtgaattg taatacgact cactataggc gcttttttttt ttttttttt    60 tttttt    66

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 2
caccacagag tctgtggaag    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
aggtgtctcg agatacttgt    20

US 6,358,681 B2

DIAGNOSTIC METHODS FOR ALZHEIMER'S DISEASE BY DETECTION OF MULTIPLE MRNAS

BACKGROUND

Alzheimer's disease (AD) is a debilitating illness that affects millions of Americans. New strategies are beginning to emerge for diagnosis of this condition, a condition that currently can only be diagnosed with certainty at autopsy. If diagnostic strategies can improve, treatment of the disease at an earlier stage, before symptoms emerge, may be possible. In fact, the only drug currently available to treat the symptoms of AD tends to be most effective if given in early stages of disease. Clearly, early and definitive diagnosis is essential.

AD is characterized clinically by cognitive decline and memory loss and neuropathologically by the presence of neurofibrillary tangles (NFTs), neuropil threads (NTs), senile plaques (SPs), and regionally specific neuronal loss (Selkoe, D. J. 1994 Annu. Rev. Cell Biol. 10:373–403; Trojanowski, J. Q. et al. 1996 In: Current Neurology, Vol. XVI, Boston: Houghton Mifflin). The gradual accumulation of paired helical filaments composed of abnormal tau in NFTs and NTs (Lee, VM-Y et al. 1991 Science 251:675–678) as well as beta-amyloid-containing fibrils within SPs (Selkoe, D. J. 1994 Annu. Rev. Cell Biol. 10:373–403) have been implicated in the pathogenesis of AD. Similar neuropathological findings also are observed in the brains of elderly Down's syndrome (DS) patients who survive beyond the fourth decade of life.

Although the molecular mechanisms responsible for the pathogenesis of NFTs, NTs, and SPs remain to be clarified, immunohistochemical and Western blot analyses of AD brains have allowed detailed characterization of the abnormal tau, beta-amyloid-containing proteins in these lesions (Arai, H. et al. 1990 Proc. Natl. Acad. Sci. USA 87:2249–2253; Arai, H. et al. 1991. Ann. Neurol. 30:686–693; Selkoe, D. J. et al. 1986. J. Neurochem. 46:1820–1834). Congo Red and analogs thereof have been used to characterize amyloid plaques in Alzheimer's brains since this fluorescent dye and analogs thereof bind to peptides that make up the fibrils of these plaques (Ashburn et al. 1996 Chemistry and Biology 3:351–358). Northern blot analyses of AD brains also have identified changes in a variety of mRNAs, including those encoding the amyloid precursor proteins (Kang, J. et al. 1987 Nature 325:733–736; Goldgaber, D. et al. 1987. Science 235:877–880; Robakis, N. K. et al. 1987. Proc. Natl. Acad. Sci. USA 84:4190–4194; Tanzi, R. E. et al. 1987. Science 235:880–884; Golde, T. E. et al. 1990. Neuron 4:253–267). Furthermore, in situ hybridization histochemistry has localized abnormal tau and amyloid precursor mRNAs to neurons and glia in the normal and AD brain (Tanzi, R. E. et al. 1987. Science 235:880–884; Golde, T. E. et al. 1990. Neuron 4:253–267; Kosik, K. S. et al. 1989. Ann. Neurol. 26:353–361; Bahmanyar, S. et al. 1987. Science 237:77–88; Schmechel, D. E. et al. 1988. Alzheim. Dis. Assoc. Disord. 2:96–111). Although other protein components in NFTs and SPs have been identified (Schmidt, M. L. et al. 1994. Exp. Neurol. 130:311–322; Strittmatter, W. J. and A. D. Roses. 1995. Proc. Natl. Acad. Sci. USA 92:4725–4727), no data are available which provide information on whether RNAs exist in NFTs and SPs themselves. In fact, little is known about the non-proteinaceous components of SPs and NFTs.

The present invention provides a method for detecting the presence of and identifying RNAs, specifically mRNAs, in NFTs, NTs, and SPs of AD brain tissue. Using this method, it has now been found that neuronal mRNAs predominate in SPs in Alzheimer's disease.

SUMMARY OF THE INVENTION

An object of the present invention is to provide a method of identifying senile plaques, neurofibrillary tangles and neuropil threads in brain tissue which comprises contacting brain tissue with a fluorescent dye capable of intercalating selectively into nucleic acids and detecting any fluorescence in the brain tissue indicative of senile plaques, neurofibrillary tangles and neuropil threads in the brain tissue.

Another object of the present invention is to provide a method of identifying RNAs in senile plaques, neurofibrillary tangles, and neuropil threads of brain tissue which encode proteins involved in the pathogenesis of Alzheimer's disease which comprises isolating single senile plaques in brain tissue by immunocytochemical techniques; identifying the presence of RNA by contacting said senile plaque with a fluorescent dye capable of intercalating selectively into nucleic acids; amplifying the identified RNA; and determining whether the amplified RNA product hybridizes to any known cDNAs for proteins involved in the pathogenesis of Alzheimer's disease.

Yet another object of the present invention is a method of diagnosing Alzheimer's disease comprising identifying the presence of RNA encoding a protein known to be involved in the pathogenesis of Alzheimer's disease.

DETAILED DESCRIPTION OF THE INVENTION

Acridine orange (AO) is a fluorescent dye that intercalates selectively into nucleic acids (Schummelfeder, N. 1958. J. Histochem. Cytochem. 6:392–393; von Bertalanffy, L. and I. Bickis. 1956. J. Histochem. Cytochem. 1956. 4:481–493; Rigler, R. 1966. Acta Physiol. Scand. 67 (Suppl.):7–122). AO histofluorescence has been used to detect RNA and DNA in malignant tumor cells as well as in cell and tissue homogenates separated by gel electrophoresis (Dart, L. H. and T. R. Turner. 1959. Lab. Invest. 8:1513–1522; McMaster, G. K. and G. G. Carmichael. 1977. Proc. Natl. Acad. Sci. USA 74:4835–4838; Pinto, A. et al. 1990. Arch. Pathol. Lab. Med. 114 (6):585–588). Cytoplasmic and nuclear RNA species also have been visualized in tissue sections of the developing and adult brain by AO histochemistry (Schmued, L. C. et al. 1982. J. Histochem. Cytochem. 30:123–128; Topaloglu, H. and H. B. Sarnat. 1989. Anat. Rec. 224:88–93; Mai, J. K. et al. 1984. J. Histochem. Cytochem. 32:97–104). Although AO also binds to mucopolysaccharides, they are not visualized in brain by AO histochemistry due to their low abundance (Szabo, M. M. and E. Roboz-Einstein. 1962. Arch. Biochem. Biophys. 98:406–412).

The affinity of AO for nucleic acids is dependent upon the concentration of the dye in the staining buffer and the pH of the solution. A low dye concentration (approximately 10–100 $\mu$g/ml) and a pH of 4.0 allows for the optimal intercalation of AO into RNA and DNA, thereby allowing the in situ visualization of these macromolecules (von Bertalanffy, L. and I. Bickis. 1956. J. Histochem. Cytochem. 1956. 4:481–493; Dart, L. H. and T. R. Turner. 1959. Lab. Invest. 8:1513–1522; Mikel, U. V. and R. L. Becker. 1991. Analyt. Quant. Cytol. Histol. 13:253–260). Specifically, upon excitation with ultraviolet/blue spectra (approximately 470–490 nm wavelength), AO intercalated into RNA emits a bright orange-red fluorescence, whereas AO intercalated into DNA emits a yellowish-green fluorescence (von Bertalanffy, L. and I. Bickis. 1956. *J. Histochem. Cytochem.* 1956. 4:481–493; Rigler, R. 1966. *Acta Physiol. Scand.* 67 (Suppl.): 7–122). In tissue sections, AO-labeled RNA and DNA stand out against the pale green background of the surrounding neuropil and white matter tracts that lack abundant nucleic acids. AO histochemistry can be used on paraffin-embedded brain sections (Topaloglu, H. and H. B. Sarnat. 1989. *Anat. Rec.* 224:88–93; Mai, J. K. et al. 1984. *J. Histochem. Cytochem.* 32:97–104), and can be combined with other histochemical/immunohistochemical techniques.

Using AO histochemistry, it has now been determined that cytoplasmic RNA species, including either ribosomal, transfer, or messenger (mRNA), are present in NFTs, NTs, and SPs of brains from AD and DS patients. AO histofluorescence was used to screen the brains of patients with AD and DS, as well as normal controls and non-AD patients with other neurodegenerative disorders, to determine whether cytoplasmic RNA species are detectable within NFTs, NTs, and SPs. In these experiments, the hippocampal formation and the entorhinal cortex were selected for analysis because NFTs, NTs, and SPs are abundant in these regions in the AD and DS brain (Hyman, B. T. et al. 1984. *Science* 225:1168–1170; Hyman, B. T. et al. 1990. *Neurology* 40:1721–1730). In addition to AO histochemistry, sections were double-labeled with AO and thioflavine-S (TS); AO histochemistry also was combined with immunocytochemistry for astrocytic and microglial markers to characterize the cellular distribution of cytoplasmic RNAs in AD brain.

Within the hippocampal formation and entorhinal cortex of normal brains, somatodendritic AO labeling of neurons was observed. AO-positive nuclei also were observed within neurons using the FITC and double cube filters. Ethanol fixation provided the most abundant and intense AO labeling in comparison to NBF and Bouin's fixed sections. Thus, using this AO labeling method cytoplasmic RNA species were identified in pyramidal cells and stellate cells within the normal aged human brain for the first time.

Cytoplasmic neuronal AO labeling also was identified within the hippocampal formation and entorhinal cortex of AD patients. However, in contrast to the control tissue intense labeling with the fluorescent dye was observed within NFTs and NTs. Specifically, AO-labeled puncta were arrayed in a filamentous pattern in NFTs and NTs throughout the hippocampal formation and entorhinal cortex. Moreover, SPs were consistently observed to contain AO labeling, both in the fibrillar corona and the core region. Upon further examination, it was found that AO-labeled NFTs and SPs were observed infrequently within the hippocampal and entorhinal cortex of the normal aged controls.

To examine the nucleic acid specificity of the AO-labeling, tissue sections were pretreated with RNase. This treatment abolished the AO labeling of NFTs, NTs, and SPs, whereas pretreatment with DNase had little or no effect upon cytoplasmic AO labeling of these lesions. Pretreatment with proteinase K also had no effect on the visualization of AO-labeled NFTs and SPs. Accordingly, it is RNA species within NFTs, NTs, and SPs which are AO-labeled.

NFTs, NTs, and SPs in DS patients also exhibited intense AO histofluoresence in the hippocampal and entorhinal regions. The distribution and density of NFTs and SPs was greater in the DS cases as compared to AD patients, however, the AO staining intensity was qualitatively similar. In contrast, AO labeling within the hippocampal formation and entorhinal cortex of the brains of patients with other neurodegenerative disease (e.g., ALS, DLDH and S-D) was similar to the pattern seen in the normal controls, with abundant cytoplasmic neuronal staining and infrequent labeling of NFTs and SPs.

To confirm that the AO-labeled profiles were indeed NFTs, NTs, and SPs, double-labeling with AO and TS was compared with adjacent single-labeled AO and TS stained sections. Qualitative observations showed that the majority of NFTs co-localized AO and TS, whereas a subpopulation of SPs contained only AO labeling. Quantitative analysis demonstrated that AO co-localized to approximately 80% of the NFTs within the stratum pyramidale of CA1 and layers II/III of entorhinal cortex. AO-stained SPs comprised approximately 55% of the entorhinal and CA1-subiculum plaques quantified.

The specificity of this AO labeling technique for NFTs, NTs and SPs thus provides a means for detecting these brain pathologies characteristic of AD in brain tissue. Further, as will be obvious to those of skill in the art upon this disclosure, while the experiments described herein are specific to acridine orange, other fluorescent dyes capable of intercalating selectively into nucleic acids could also be used. Examples of other nucleic acid binding dyes include, but are not limited to bis-benzimide, ethidium bromide and ethidium homodimer. It is believed that these fluorescent dyes, and in particular AO, labeled with a reporter molecule in accordance with well known techniques, could be used in vivo in the diagnosis of Alzheimer's disease in patients suspected of suffering from this diseases by detecting dye bound to NFTs, NTs and SPs in the brain of these patients.

The method of the present invention has been used to identify RNAs within NFTs, NTs, and SPs of AD and DS patients, which play a role in the pathogenesis of these hallmark AD lesions. An amplification RNA (aRNA) technique (Eberwine, J. et al. 1992. *Proc. Natl. Acad. Sci.* 89:3010–3014; Eberwine, J. et al. 1995. *The Neuroscient.*1:200–211; VanGelder, R. et al. 1990. *Proc. Natl. Acad. Sci. USA* 87:1663–1667) was used that allows identification and quantitation of multiple mRNAs of variable abundance in single immunocytochemically identified cells (Crino, P. B. and J. Eberwine. 1996. *Neuron* 17:1173–1187; Crino, P. B. et al. 1996. *Proc. Natl. Acad. Sci. USA* 93:14152–14157), as well as a method for the analysis of multiple DNA sequences from single cells in fixed tissue sections (Becker, I. et al. 1996. *Lab. Invest.* 75:801–807; D'Amore, F. et al. 1997. *Lab. Invest.* 76:219–224; Emmert-Buck, M. R. et al. 1996. *Science* 274:998–1001) and in situ hybridization. The presence of RNA in SPs was verified by AO histofluoresence as before, and mRNAs from individual, immunocytochemically identified SPs were amplified. The amplified products were then hybridized to known cDNAs on reverse Northern blots. By "known cDNAs" is meant cDNAs encoding proteins which have been implicated in the pathogenesis of plaques, tangles, or the degeneration of neurons in AD. Examples include, but are not limited to, cDNAs corresponding to the following classes of proteins: 1) plaque-associated proteins (amyloid-beta protein precursor, presenilin 1, heparin sulfate proteoglycan); 2) cytoskeletal proteins (tau, high, low and medium molecular weight neurofilament subunits, beta-actin, microtubule-associated proteins, nestin); 3) protein kinases and phosphatases (PP1-alpha, PP1-gamma, PP2-alphac, cyclin-dependent kinase, glycogen synthase kinase 3 beta); 4) neurotrophins and neurotrophin receptors; 5) glial enriched proteins (glial fibrillary acidic protein, apolipoprotein E, alpha 1-antichymotrypsin, interleukins); 6) transcriptional activators/cell death mediators (cyclic AMP response element binding protein, c-fos, c-jun, cyclin D1); 7) glutamate receptors and calcium channels; and 8) others (superoxide dismutase 1, dopamine-beta hydroxylase, glutamate decarboxylase, and glyceraldehyde-3'-phosphate dehydrogenase).

Due to its consistent high abundance in SPs, cyclic AMP response element binding protein mRNA (CREB mRNA) was used to normalize the hybridization signal to other mRNAs on each blot, enabling quantitative comparisons of the relative mRNA levels in individual SPs with the mRNA levels in the neurons and neuropil of CA1 in elderly control brains. Empty vector was used as a negative control. Following CREB mRNA normalization, SPs were shown to harbor two distinct populations of mRNAs, high abundance and low abundance mRNAs. There were 18 high abundance mRNAs identified including amyloid-beta protein precursor (APP), tau, bcl-2, bax, PP1-alpha, PP1-gamma, and six different AMPA/kainate glutamate receptor mRNAs. There were 33 low abundance mRNAs identified that included neurofilament subunit mRNAs and glial enriched mRNAs. Comparison of mRNAs amplified from SPs as well as CA1 neurons and neuropil revealed some distinct differences. For example, bax mRNA, which encodes a protein that promotes apoptotic cell death by interacting with the anti-apoptotic bcl-1 protein, was present in SPs at significantly higher levels than in control CA1 neurons and neuropil. It is known that bax expression is upregulated in the AD brain (MacGibbon, G. A. et al. 1997. *Brain Res.* 750:223–234; Su, J. H. et al. 1997. *J. Neuropathol. Exp. neurol.* 56:86–93). In contrast, the mRNA levels of high affinity nerve growth factors, trkB and trkC, were significantly lower in SPs compared to control CA1 neurons, a finding that is paralleled by evidence that neurotrophin signaling may be impaired in AD due to diminished expression of neurotrophin receptors (Salehi, A. et al. 1996. *Neurosci.* 75:373–387; Mufson, E. J. et al. 1997. *Exp. Neurol.* 146:91–103). Several mRNAs preferentially enriched in glia (alpha 1-act, APOE, GFAP, and IL-1) and a housekeeping gene (GAPDH) were also consistently less abundant in SPs relative to control neuropil.

In situ hybridization was then used to localize selected mRNAs detected in SPs by the aRNA method to SPs in tissue sections. The presence of CREB mRNA in SPs was confirmed using a digoxigenin labeled CREB probe; and CREB mRNA was shown to be distributed throughout the corona of hippocampal SPs double-labeled with TS. Digoxigenin labeled CREB also was observed in neurons, but not in vascular amyloid deposits. Because amyloid beta is the major component of amyloid precursor plaques, and APP mRNAs have been localized to TS stained SPs by in situ hybridization (Hyman, B. T. et al. 1993. *Mol. Brain Res.* 18:253–258), detection of APP mRNA in SPs, CA1 neurons, and neuropil was performed by PCR. The PCR primers used differentially recognize the most abundant isoforms of APP in brain ($APP_{695}$, $APP_{751}$, and $APP_{770}$). $APP_{695}$, the splice variant enriched within neurons, was the predominant species of APP detected in single SPs, CA1 neurons, and neuropil. To confirm the identity of the 87 base pair PCR product obtained from single SPs and CA1 neurons, this PCR product was sequenced and shown to be 100% identical to the corresponding segment of wild type $APP_{695}$. This confirms that the individual mRNAs amplified from single SPs, neurons and the neuropil correspond to the cDNAs used to detect and identify these same mRNAs. Accordingly, using the method specific characterization of mRNA species sequestration in AD SPs can be performed.

Further, multiple mRNA species have now been found in individual, extracellular SPs of the AD hippocampus with this method combined with aRNA expression profiling, PCR and in situ hybridization methods. The expression profile of mRNAs amplified from these SPs is predominantly neuronal. Thus, using this method of the present invention, studies can be performed to explore the role of these mRNAs in the pathogenesis of AD as well as to identify brains with AD specific changes. Further, expression profiling information derived from the method of the present invention can be used in the design of probes specific to identified mRNA encoding proteins involved in the pathogenesis of AD. Such probes can be used in vivo to detect abnormal levels of these mRNAs which may be an early indicator of AD. The existence of a variety of specific mRNAs in AD brain is also a potential tool for use in designing new therapeutics to be used in the treatment of AD.

The following non-limiting examples are presented to further illustrate the present invention.

EXAMPLES

Example 1: Tissue Preparation

Postmortem samples containing the hippocampal formation and entorhinal cortex were dissected from approximately 1 cm-thick coronal brain slabs of 13 AD, 5 DS, 8 age-matched control and 7 non-AD patients with neurodegenerative disease and processed. Tissue samples were immersion fixed in either 70% ethyl alcohol containing 150 mM sodium chloride, 10% neutral buffered formalin, or Bouins solution for 24 hours at 22° C., embedded in paraffin, and 6 μm thick serial sections were cut.

Example 2: Acridine Orange Histochemistry

A protocol for AO histochemistry was developed using human postmortem tissues embedded in paraffin based on the procedures of von Bertalanffy and Bickis (1956; *J. Histochem. Cytochem.* 4:481–493) and Mikel and Becker (1991; *Analyt. Quant. Cytol. Histol.* 13:253–260). Briefly, tissue sections were deparaffinized in xylene, graded through a descending ethanol series, and placed in distilled water for 5 minutes. The sections were placed in a 0.2 M dibasic sodium phosphate/0.1 M citric acid solution (pH 4.0) for 5 minutes prior to staining with AO (10 μg/ml; Sigma Chemical Co.) for 15 minutes. The sections were rinsed three times in dibasic sodium phosphate/citric acid buffer, immersed in 50% ethanol in phosphate-buffered saline (0.12 M, pH 7.4) for 2 minutes, cleared in xylene, and mounted with an anti-fading medium (Vectashield, Vector Laboratories). To reduce the intense autofluorescence of lipofuscin granules that are abundant in the senescent human brain, selected tissue sections were pretreated with 0.05% potassium permanganate in PBS for 20 minutes followed by 0.2% potassium metabisulfite/0.2% oxalic acid in PBS for 30 seconds prior to AO histochemistry. Control experiments included no staining or preincubation of the tissue sections for 60 minutes with RNase (0.5 μg/μl, Boehringer Mannheim), DNase (10 U/μl, Boehringer Mannheim), and proteinase K (1 µg/µl, Sigma Chemical Co.) in dibasic sodium phosphate/citric acid buffer at 36° C. in a humidified chamber prior to AO histochemistry.

Example 3: Double Label Histochemistry

To better delineate AO labeling within NFTs, NTs, and SPs, selected sections were double-labeled with AO and TS. AO histochemistry was performed as described above followed by immersion in 0.0125% TS (Sigma Chemical Co.) in a 40% EtOH/60% PBS solution in the dark for 2 minutes. The procedure also was performed in reverse order to control for staining efficacy. Adjacent sections were stained with AO or TS alone for comparison with double label preparations.

To determine if AO labeling was localized to astrocytes or microglia associated with SPs, another double label procedure was employed. Briefly, deparaffinized tissue sections were quenched with methanol and 5% hydrogen peroxide for 30 minutes and washed in running water for 10 minutes. The sections were blocked in 2% horse serum in Tris/HCl buffer (pH 7.6) for 1 hour and incubated with monoclonal antibodies specific for the astrocyte marker glial fibrillary acidic protein (GFAP; 2.2B10; 10 µg/µl; Lee, VM-Y et al. 1984. *J. Neurochem.* 42:25–32) or the macrophage marker CD68 (10 µg/µl Dako Corporation) in Tris buffer overnight at 4° C. in a humidified chamber. Sections were processed using the peroxidase-antiperoxidase method and developed with 0.05% diaminobenzidine, 0.03% hydrogen peroxide and 0.01 M imidazole in Tris buffer for 10 minutes (Schmidt, M. L. et al. 1987. *Lab. Invest.* 56:282–294). After three washes in Tris buffer, the tissue sections were processed for AO histochemistry as described above. Adjacent sections were also prepared for controls using single label GFAP and CD68 immunocytochemistry.

Example 4: Quantitation of Staining/Binding

Tissue sections were visualized with a Nikon FXA photomicroscope equipped with epifluorescence and brightfield optics. For fluorescence observation, three interference filters were used: Nikon G-2A rhodamine filter for AO (RNA) labeling, Nikon B-2E fluorescein isothiocyanate (FITC) filter for TS labeling, and a FITC/Texas Red double-cube filter (51006V3, Chroma Technology Corporation) for simultaneous fluorescence labeling.

A quantitative scheme was designed (see Ginsberg, S. D. et al. 1995. *Neuroscience* 65:563–575) to assess the percentage of NFTs and SPs that contained AO labeling relative to TS-labeled profiles. Briefly, fluorescent microscope images were digitized to a computer workstation where actual quantification was performed using a morphometric software package (Northern Exposure, Phase III Imaging Systems). Six non-overlapping fields (500 µm×500 µm) were analyzed at 40× (1.3 numerical aperture) within the stratum pyramidale of CA1 and layers II/III of entorhinal cortex in three tissue sections from each of four AD patients, for a total of 144 fields. In these studies, the TS-labeled image was digitized and quantified first, followed by the AO-labeled image within the same x and y axes as the TS-labeled image. The number of AO-labeled profiles was reported as a proportion of TS-labeled profiles. Results showed that RNA was specifically sequestered within Sps, NFTs, and NTs in AD brain.

Example 5: Quantification of Multiple mRNAs

Single immunocytochemically identified cells were used. Tissue was from 6 µm-thick fixed (70% EtOH plus 150 mM NaCl) paraffin-embedded tissue sections of the hippocampus (postmortem samples). AD tissues were immunostained with antibodies directed against amyloid beta (R2332) or hyperphosphorylated tau (PHF1), and control sections were immunostained with an antibody directed against phosphorylated NF proteins (RmdO20; NF–H+/NF–M+).

The presence of RNA was verified by AO histofluorescence as described above, and mRNAs from individual SPs were amplified. For amplification, an oligonucleotide primer consisting of 24 TTPs coupled to a T7 RNA polymerase promoter sequence (oligo-(24)T7;AAACGACGGCCAGTGAATTGTAATACGACTCACTATAGCG CTTTTTTTTTTTTTTTTTTTTTTTT) (SEQ ID NO.1), was hybridized to cellular poly (A+) mRNA directly on hippocampal sections (in situ transcription) containing immunolabeled SPs and/or CA1 neurons for 18 hours in 50% formamide (Eberwine, J. et al. 1992. *Proc. Natl. Acad. Sci. USA* 89:3010–3014; Eberwine, J. et al. 1995. *The Neurosci.* 1:200–211; van Gelder, R. et al. 1990. *Proc. Natl. Acad. Sci. USA* 87:1663–1667; Crino, P. B. and J. Eberwine. 1996. *Neuron* 17:1173–1187; Crino, P. B. et al. 1996. *Proc. Natl. Acad. Sci. USA* 93:14152–14157). cDNA was synthesized directly on the section with avian myeloblastosis virus reverse transcriptase (AMVRT, 0.5 U/µl, Seikagaku America, USA) in Tris-HCl buffer (pH 8.3) with $MgCl_2$ (6 mM), KCl (120 mM), dithiothreitol (7 mM), dNTPs [dATP, dCTP, dGTP, TTP (250 µM)], and 0.12 U/µl RNAsin. Individual SPs and CA1 neurons were dissected from surrounding neuropil via a micromanipulator and collected in 1.5 mm OD glass micropipettes backfilled with electrode buffer (to assure cDNA synthesis; 10 mM HEPES buffer (pH 7.4) with dNTPs (250 µM), oligo-dT(24)T7 primer, and AMVRT. cDNA synthesis was performed in 1.5 mm microfuge tubes for 90 minutes at 42° C. (Eberwine, J. et al. 1992. *Proc. Natl. Acad. Sci. USA* 89:3010–3014; Eberwine, J. et al. 1995. *Neurosci.* 1:200–211; van Gelder, R. et al. 1990. *Proc. Natl. Acad. Sci. USA* 87:1663–1667; Crino, P. B. and J. Eberwine. 1996. *Neuron* 17:1173–1187; Crino, P. B. et al. 1996. *Proc. Natl. Acad. Sci. USA* 93:14152–14157). mRNA was amplified (aRNA) from double stranded cDNA template with T7 RNA polymerase (Epicentre Technologies, USA). Two rounds of amplification (final amplification approximately 1×106 fold from the original message) were performed by the aRNA method, and the second round of amplification incorporated $^{32}P$ CTP into the amplified products.

This amplification was followed by hybridization of the amplified products to known cDNAs on reverse Northern blots. Briefly, Radiolabeled aRNA from single SPs, CA1 neurons, and neuropil was used as a probe to linearized plasmid cDNAs adherent to nylon membranes (Hybond, Amersham, USA) for reverse Northern (slot) blots (48 cDNA clones per blot). Prehybridization (12 hours) and hybridization (48 hours) consisted of 6× SSPE, 5× Denhardt's solution, 50% formamide, 0.1% sodium dodecyl sulfate, and denatured salmon sperm DNA (200 µg/ml) at 42° C. (Eberwine, J. et al. 1992. *Proc. Natl. Acad. Sci. USA* 89:3010–3014; Eberwine, J. et al. 1995. *The Neurosci.*

1:200–211; van Gelder, R. et al. 1990. *Proc. Natl. Acad. Sci. USA* 87:1663–1667; Crino, P. B. and J. Eberwine. 1996. *Neuron* 17:1173–1187; Crino, P. B. et al. 1996. *Proc. Natl. Acad. Sci. USA* 93:14152–14157). Blots were washed in 2×, 1×, and 0.5× SSC and apposed to phosphoscreens for 48 hours. Hybridization intensity was quantified with densitometic software (ImageQuant, Molecular Dynamics, USA). cDNAs were selected for analysis based on the implication of the corresponding proteins in some part of the AD pathogenic process.

SPs were shown to contain two distinct populations of mRNAs, high abundance mRNAs and low abundance mRNAs. To confirm these findings, in situ hybridization was used to localize the selected mRNAs detected in SPs. Tissue sections pretreated with proteinase K (10 µg/ml) prior to acetylation with 0.2% acetic anhydride were hybridized with DIG-UTP-labeled cRNA antisense probes to CREB in hybridization buffer (50% formamide, 10% dextran sulfate, 4× SSC, 1× Denhardt's solution, 500 µg/ml denatured salmon sperm DNA, and 250 mg/ml yeast tRNA) for 16 hours at 50° C. CREB mRNA was visualized with anti-DIG antibodies (Boehringer Mannheim, USA) with NBT/BCIP (Boehringer) substrate solution as per manufacturer's specifications. Control (cold competition) experiments included the addition of 50-fold excess of unlabeled CREB cRNA to sections in hybridization buffer for 12 hours prior to the addition of DIG-labeled CREB cRNA probe and development as above. Sections were subsequently stained with TS (Sigma, USA; 0.0125% in 60% phosphate-buffered saline/40% ethanol) and coverslipped with antifade medium. The results confirmed that mRNA was present in SPs and was distributed throughout the corona of hippocampal SPs.

Because amyloid-beta is the major component of SPs, and amyloid protein precursor protein (APP) mRNAs were found to be localized to Sps, PCR techniques were used to detect APP mRNAs in Sps. PCR was performed (sense primer, 5'-CACCACAGAGTCTGTGGAAG-3', (SEQ ID NO. 2), corresponding to bp 958–977 of the $APP_{751}$ gene and antisense primer, 5'-AGGTGTCTCGAGATACTTGT-3', (SEQ ID NO. 3), corresponding to bp 1194–1213 of $APP_{751}$) using aRNA template double stranded DNA from SPs, CA1 neurons and neuropil. PCR conditions were 35 or 28 cycles [denaturation (4 minutes at 90° C.); annealing (1 minute at 55° C.); elongation (2 minutes at 72° C.); $MgCl_2$ (4 mM)] and PCR products were visualized on 1.5% agarose gels stained with ethidium bromide. The 312, 255, and 87 bp fragments correspond to $APP_{770}$, $APP_{751}$, and $APP_{695}$, respectively. The 87 bp fragment was ligated into p-GemT vector (Promega, USA), transfected into DH5α cells, and sequenced. Results showed that APP695 was the predominant species of APP detected in single SPs, CA1 neurons, and neuropil.

What is claimed is:

1. A method of identifying cytoplasmic RNAs in senile plaques, neurofibrillary tangles, and neuropil threads of brain tissue taken from a hippocampal region or an entorhinal cortex of a brain, wherein said cytoplasmic RNAs encode proteins involved in the pathogenesis of Alzheimer's disease comprising:

(a) isolating single senile plaques in brain tissue by immunocytochemical techniques;
   (b) identifying the presence of cytoplasmic RNA by contacting said senile plaque with a fluorescent dye capable of intercalating selectively into cytoplasmic RNAs present in said brain tissue;
   (c) amplifying the identified RNA; and
   (d) determining whether the amplified RNA product hybridizes to any known cDNAs for proteins involved in the pathogenesis of Alzheimer's disease.

2. A method of detecting the presence of cytoplasmic messenger RNA in senile plaques, neurofibrillary tangles, and neuropil threads of brain tissue taken from a hippocampal region or an entorhinal cortex of a brain wherein said messenger RNA encodes a protein involved in the pathogenesis of Alzheimer's disease comprising:

a) isolating single senile plaques in brain tissue by immunocytochemical methods;
   b) identifying the presence of RNA by contacting said senile plaque with a fluorescent dye capable of intercalating selectively into cytoplasmic RNAs present in said brain tissue;
   c) amplifying said RNA; and
   d) hybridizing the amplified RNA product to a known cDNA for a protein involved in the pathogenesis of Alzheimer's disease.

* * * * *